United States Patent
Van De Spijker

(10) Patent No.: US 6,518,762 B2
(45) Date of Patent: Feb. 11, 2003

(54) DEVICE FOR STABILIZING PARTS OF A BODY PARTICULARLY FOR COMPUTED TOMOGRAPHY DIAGNOSTICS

(75) Inventor: Arnoldus Johannes Gerardus Emmanuel Van De Spijker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/024,765

(22) Filed: Dec. 20, 2001

(65) Prior Publication Data

US 2002/0079898 A1 Jun. 27, 2002

(30) Foreign Application Priority Data

Dec. 22, 2000 (EP) .............................. 00204792

(51) Int. Cl.$^7$ ................................ G01V 3/00
(52) U.S. Cl. ....................... 324/318; 324/322
(58) Field of Search ................ 324/318, 322, 324/314, 309, 307, 311, 312; 128/653.5

(56) References Cited

U.S. PATENT DOCUMENTS 5,379,768 A * 1/1995 Smalen ..................... 324/318
5,617,027 A * 4/1997 Decke ....................... 324/318
5,945,827 A * 8/1999 Gronauer et al. ........... 324/318
6,144,203 A   11/2000 Richard et al. ............. 324/318

* cited by examiner

*Primary Examiner*—Edward Lefkowitz
*Assistant Examiner*—Brij B. Shrivastav
(74) *Attorney, Agent, or Firm*—John Vodopia

(57) ABSTRACT

The invention relates to a stabilization device for stabilizing parts of a body during imaging diagnostics performed by means of magnetic resonance, for example computed tomography. The stabilization device includes a flexible RF coil (6) which is pressed against the part of the body to be examined by way of a supporting element (1). The stabilization device in accordance with the invention is distinct from customary stabilization devices that must be applied by a third party and often have to be fixed by means of belts in that the supporting element (1) is constructed so as to be adapted to the part of the body to be stabilized and also so as to be elastically compliant, and that the coil (6) is connected to the supporting element (1) in such a manner that it follows the elastic deformation thereof and hence is self-adapting. The coil is preferably embedded in a pillow (2) which is connected to the supporting element that is provided with a plurality of spring elements (3) that are movable independently of one another.

9 Claims, 2 Drawing Sheets

Figure 1:
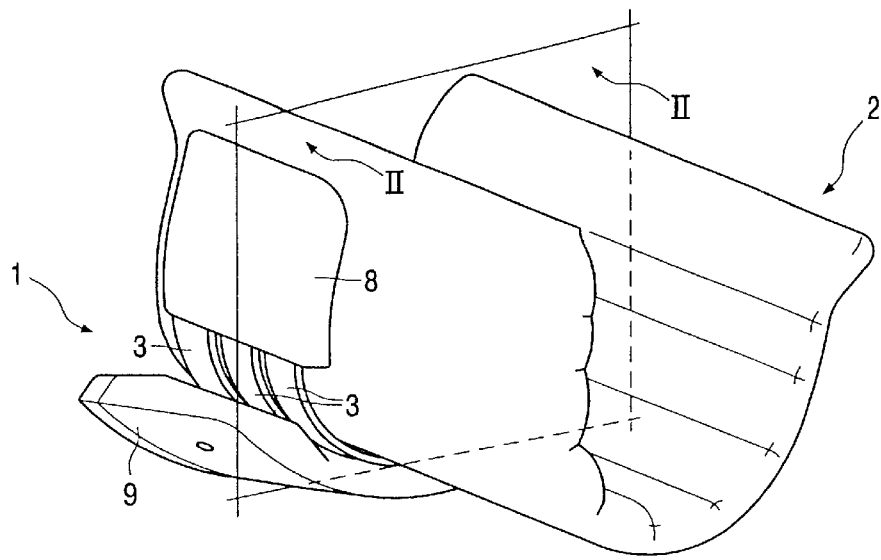

DEVICE FOR STABILIZING PARTS OF A BODY PARTICULARLY FOR COMPUTED TOMOGRAPHY DIAGNOSTICS

The invention relates to a stabilization device for use during imaging diagnostics performed on parts of a body by means of magnetic resonance, notably computed tomography or magnetic resonance tomography as disclosed in the introductory part of claim 1.

For computed tomography examinations of parts of a body it is necessary to arrange a coil for building up an electromagnetic field, that is, a so-called high-frequency or RF coil, at a small, uniform distance from the part of the body to be examined and the part of the body concerned generally requires stabilization so as to keep it as steady as possible during the examination. Therefore, U.S. Pat. No. 5,617,027 discloses a stabilization device of this kind where a flexible coil is pressed against the part of the body to be examined after which it is fixed in place and stabilized by way of a vacuum pillow that is arranged around the part of the body and the coil. In order to obtain the desired position, first the coil and subsequently the pillow must be manually adapted to the part of the body and be held until the air is evacuated from the pillow. Stability is ensured only after such evacuation. This system has the drawback that the operation of fitting the coil and the vacuum pillow and evacuating the pillow must be performed by skilled staff and requires a comparatively long period of time.

Also known are simpler systems where the flexible coil is arranged around the part of the body and is secured by means of a fixing strap with a catch or a buckle. However, such systems must also be fitted by skilled personnel and are often experienced as being uncomfortable by the patient. It is notably in the case of examinations in the region of the head or the neck that such straps that include catches and are fitted around the neck can be very uncomfortable. Moreover, such fixing of the coil has no stabilization effect whatsoever.

Therefore, it is an object of the invention to provide a stabilization device of the kind set forth which enables fast and reliable adaptation of the coil to the part of the body to be examined and at the same time provides adequate stabilization thereof.

This object is achieved by means of a stabilization device as disclosed in the characterizing part of claim 1. As a result of the use of a supporting element whose shape has already been adapted to the part of the body to be examined but is still elastic and the connection of the coil to this supporting element in such a manner that the coil always follows the shape of the supporting element and is deformed together therewith, the coil is automatically pressed uniformly but comfortably against the part of the body when the part of the body is introduced into the stabilization device, that is, without assistance from staff being required.

In order to enhance the comfort, the coil should preferably be embedded in a flat pillow. This pillow can project at least partly from the supporting element in as far as it has enough stability of its own to keep it from hanging down directly to the side of the supporting element. A device of this kind is preferably used for parts of the body that need stabilization in given regions only. For example, the supporting element may be provided merely in the region of the neck of a patient whereas the pillow with the coil is also present in the transitional zone between the neck and the shoulders; this zone does not require further stabilization, because the pillow alone has no (or in any case only a slight) stabilization effect in the region in which it projects from the supporting element.

The supporting element of the stabilization device can be particularly advantageously provided with spring elements that are adapted to the curvature and shape of the part of the body to be stabilized. The elasticity of the device and the necessary strength of the stabilization effect can be adjusted by the choice of the resilience or the material of the spring elements.

In sub-regions in which strong stabilization is required or even no compliance of the spring elements is desired, these elements can be supported by a correspondingly shaped rigid basic member.

In order to enable an as individual as possible and possibly also a locally different adaptation to the part of the body to be stabilized, it is advantageous to arrange a plurality of spring elements adjacent one another and to construct these elements as fingers, each time one end of the spring element being fixed while its other end is freely resilient. This offers automatic and strict adaptation of the stabilization device in combination with a particularly high degree of comfort.

In order to protect the coil and to establish the connection between the coil and the supporting element the coil is preferably accommodated in a sleeve which is provided with one or more receiving pockets that are detachably entered by the supporting element. The coil can thus be removed from the supporting element, for example for the purpose of cleaning, and the coil and the supporting element can be exchanged independently of one another. In as far as the coil is embedded in a pillow as described above, the pillow is preferably arranged in the sleeve together with the coil.

The stabilization device in accordance with the invention is particularly suitable for forming a neck support, because the automatic adaptation that takes place directly when the neck and the head of the patient are arranged thereon is experienced as being particularly pleasant whereas manual adaptation and fixation by means of belts, vacuum pillows or the like is particularly annoying at this area.

Figure 2:
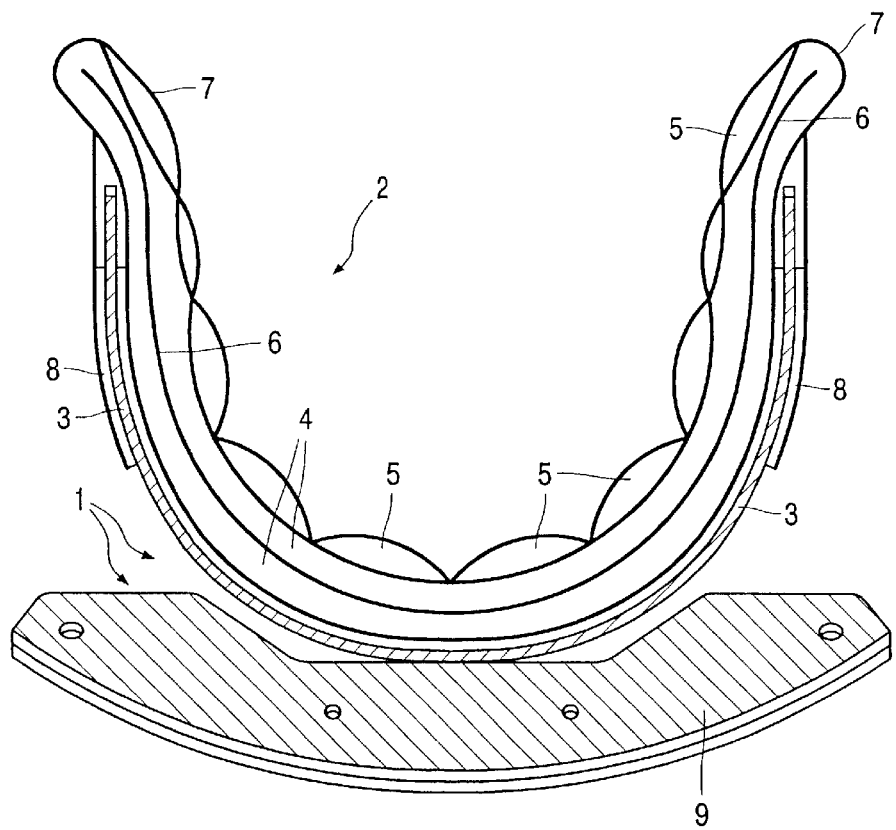
Figure 3:
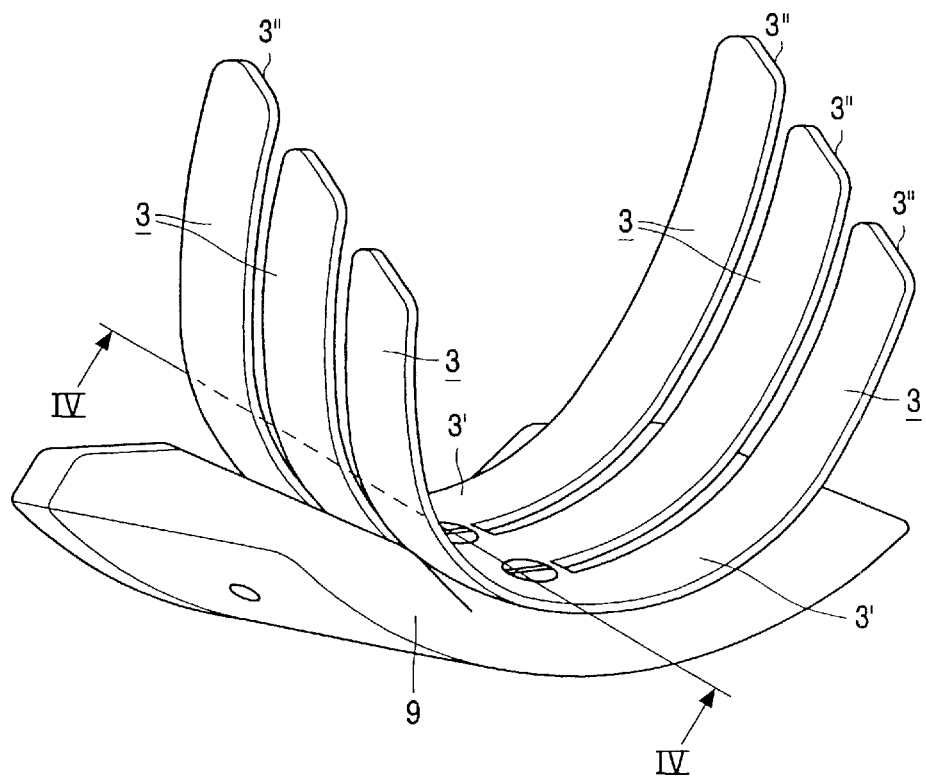
Figure 4:
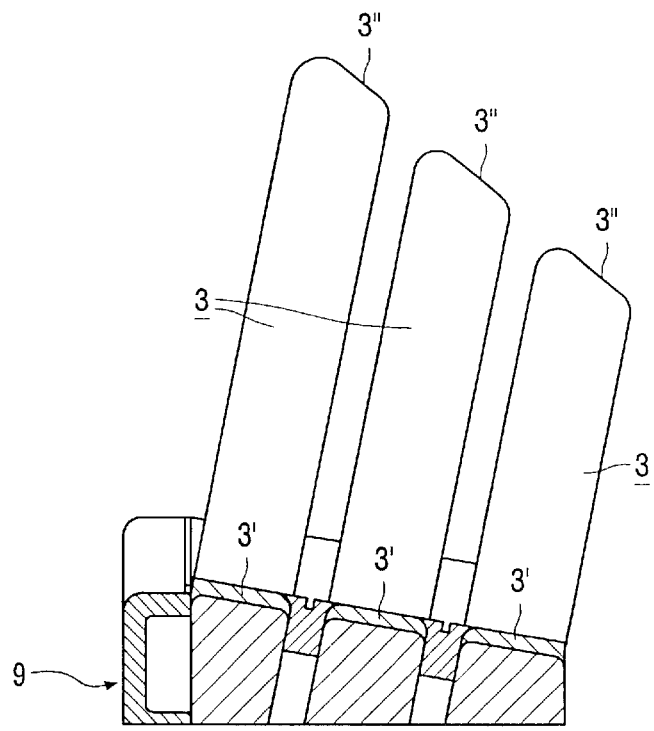

Further advantages and details will become apparent from the dependent claims and an embodiment of the invention that is shown in the drawings; therein:

FIG. 1 is a perspective view of a stabilization device in accordance with the invention, FIG. 2 is a cross-sectional view, taken in the plane II—II, of the device shown in FIG. 1, FIG. 3 shows the supporting element of the device of FIG. 1 without a pillow and a coil, and FIG. 4 is a sectional view, taken along the line IV—IV, of the element of FIG. 3.

The stabilization device that is shown in the FIGS. 1 and 2 is a neck support and consists of a supporting element 1 and a pillow 2 which is connected thereto and projects from the supporting element 1 in the transitional zone between the neck and the shoulder of the patient to be examined; the pillow is readily and flexibly adaptable without having a stabilizing effect in this zone whereas the region of the neck near the transition to the head is stabilized by elastically compliant spring elements 3 of the supporting element.

The construction of the device is illustrated notably in the cross-sectional view of FIG. 2. It can be seen that a flexible electromagnetic coil 6 is embedded in the pillow 2 which consists of two flexible foam plates 4 and a plurality of foam pads 5. The pillow 2 and the coil 6 are enclosed by a sleeve 7. The sleeve 7 is provided with pockets 8 at both sides, the spring elements 3 are inserted into said pockets by way of their free ends 3". The connection between the coil 6 and the supporting element 1 is thus established and it is ensured that the pillow and the coil always follow the motion of the spring elements 3.

The FIGS. 3 and 4 illustrate the construction of the supporting element 1. The embodiment shown is provided with six finger-like spring elements 3, one end 3' of which is fixed whereas the other end 3" is constructed so as to be freely resilient.

In order to support the spring elements 3 and to limit their elastic movement at least in the lower region, the spring elements are attached to an essentially rigid basic member 9.

The basic member 9 and the spring elements 3 of the embodiment shown preferably are made of polycarbonate whereas the foam plates 4 and the foam pads 5 are preferably made of polyester and the sleeve 7 notably of polyurethane foil.

The stabilization device in accordance with the invention offers a high degree of comfort to the patient to be examined and is fully self-adaptive, so that no further staff is required for this purpose.

What is claimed is:

1. A stabilization device for use during imaging diagnostics performed on parts of a body by means of magnetic resonance, which device includes a supporting element (1) and at least one flexible RF coil (6) that is to be pressed against the part of the body by the supporting element, characterized in that the supporting element (1) is constructed so as to be adapted to the part of the body to be stabilized and elastically compliant as well, and that the coil (6) is connected to the supporting element (1) in such a manner that it follows the elastic deformation thereof.

2. A stabilization device as claimed in claim 1, characterized in that the coil (6) is embedded in a pillow (2).

3. A stabilization device as claimed in claim 2, characterized in that the pillow (2) projects at least partly from the supporting element (1) and has an inherent stability that suffices for this purpose.

4. A stabilization device as claimed in claim 1, characterized in that the supporting element (1) comprises spring elements (3) that are adapted to a curvature of the part of the body to be stabilized.

5. A stabilization device as claimed in claim 4, characterized in that the spring elements (3) are supported at least in given areas by a rigid basic member (9) that corresponds to the curvature of the spring elements (3).

6. A stabilization device as claimed in claim 4, characterized in that a plurality of spring elements (3) are arranged adjacent one another and have a finger-like construction, each time one end (3') of the spring elements (3) being fixed whereas the other end (3") is freely resilient, independently of the other spring elements (3).

7. A stabilization device as claimed in claim 1, characterized in that the coil (6) is arranged in a sleeve (7) which includes at least one receiving pocket (8) that can be detachably entered by the supporting element (1).

8. A stabilization device as claimed in claim 6, characterized in that the free ends (3") of the spring elements (3) project into the receiving pocket (pockets) (8).

9. A stabilization device as claimed in claim 1, characterized in that it is constructed as a neck support.

* * * * *